United States Patent
Ansley

(10) Patent No.: US 6,719,984 B1
(45) Date of Patent: Apr. 13, 2004

(54) COMPOSITION AND METHOD FOR IMMUNOMODULATION IN MAMMALS

(76) Inventor: Daniel R. Ansley, 404 S. Maple St., Ottawa, KS (US) 66067

( * ) Notice: Subject to any disclaimer, the term of this patent is extended or adjusted under 35 U.S.C. 154(b) by 0 days.

(21) Appl. No.: 09/666,010

(22) Filed: Sep. 19, 2000

(51) Int. Cl.⁷ .............................................. A61K 39/39
(52) U.S. Cl. ..................... 424/278.1; 424/531; 514/12; 514/21; 514/885; 530/830
(58) Field of Search .............................. 424/531, 278.1; 514/885, 2, 12, 21; 530/830

(56) References Cited

U.S. PATENT DOCUMENTS

| | | | |
|---|---|---|---|
| 4,702,908 A | * | 10/1987 | Thorbecke et al. ........... 424/88 |
| 5,086,164 A | * | 2/1992 | Maione et al. .............. 530/324 |
| 5,219,578 A | * | 6/1993 | Ansley ........................ 424/531 |
| 5,464,816 A | * | 11/1995 | Nagai et al. .................... 514/2 |

OTHER PUBLICATIONS

Fraser et al (eds), The Merck Veterinary Manual, Seventh Edition, Merck & Co., Inc., 1991, pp. 39, 195–197, 248–250, 723–724, 854–855.*
Herbert et al, Dictionary of Immunology—3CDED, Blackwel Scientific Publications, 1985, p. 218.*

* cited by examiner

*Primary Examiner*—David Saunders
(74) *Attorney, Agent, or Firm*—Serle Ian Mosoff

(57) ABSTRACT

This invention relates to compositions and processes utilized to modulate the immune system of mammals. More particularly, the present invention relates to the use of low molecular weight substantially immunoglobulin free fractions isolated from mammals to induce a stimulated immune response in mammals.

7 Claims, 3 Drawing Sheets

COMPOSITION AND METHOD FOR IMMUNOMODULATION IN MAMMALS

BACKGROUND OF THE INVENTION

It has long been known that mammals, when confronted with bacterial or viral infections, exhibit efforts at self-healing which are initiated by a complex physiological network referred to as the immune system. The immune system operates in response to a challenge to the mammal by initially recognizing the presence of a foreign organism or pathogen within the animal's body. In mammals, this is followed by an attack on the foreign organism by the neutrophils, macrophages and other "killer" cells of the immune system. This immune response functions or is "turned on" by a variety of immune system regulators which activate the various aspects of the immune system depending upon the type of insult confronting the subject animal.

A substantial component of the immune system is a group of structurally related glycoproteins, collectively known as immunoglobulins, contained within blood and extra cellular fluids. Five immunoglobulin classes have been identified. Immunoglobulin G (IgG), IgM, IgA, IgD and IgP. The basic structural unit of each immunoglobulin class consists of two pairs of polypeptide chains joined by disulfide bonds. The five classes of immunoglobulins have different biological properties and different distributions in the body. The structure responsible for the biological properties of each immunoglobulin class is located on that part of the immunoglobulin molecule which is unique for each class—the Fc fragment. While some antibodies are produced at all times in normal animals, other antibodies are produced only in response to specific antigenic stimulation (e.g., when pathogenically challenged).

IgG is the major antibody class in normal mammalian systems and forms about 70% of the total immunoglobulin. IgG is evenly distributed between intra- and extra vascular pools. It is the first major antibody of the secondary immune response and belongs to the exclusive antitoxin class. IgG is a monomeric protein which can be divided into four sub-chains—two heavy chains "H" and two light chains "L". Taking the four sub-chains together each IgG molecule consists of one $H_2L_2$ unit with a molecular weight of approximately 140,000 Daltons. Molecules of the IgG class are actively transported across the placenta and provide passive immunity to newborns at a time when the infant's immune mechanisms are not developed.

The remaining four immunoglobulin classes are more narrow components of the immune system.

IgM is the first immunoglobulin class produced by the maturing fetus. IgM does not normally cross the placenta from the mother to fetus, but may be produced actively by the fetus prior to birth, especially if the fetus has been exposed to antigens by infection. IgA is found in relatively small amounts in serum and tissue fluids, but is present in high concentrations in external secretion such as saliva, tears, and bronchial secretions. IgE is also present in very low concentrations and appears to be associated with the histamine response. The last immunoglobulin class, IgD, is present in very low concentrations in secretions. IgD stimulates immature lymphocytes to multiply and differentiate thereby causing the production and secretion of other antibodies. Therefore, all immunoglobulin classes are important in immune system responses.

Modulation of the immune system to effect greater response to foreign agents has been an area of interest for some years. The development of specific antibodies through vaccination has long been utilized to provide mammals with long term immune defense mechanisms to specific microorganism forms.

Ansley, U.S. Pat. No. 5,219,578, Jun. 15, 1993 discloses a caprine serum fraction consisting principally of non-adjuvanted IgG. This IgG fraction is useful as an immunostimulant in mammals when challenged by specified diseases.

Recent efforts in immunology have been directed towards the utilization of immune system regulating molecules, rather than one of the five classes of immunoglobulins, to provide increased immune system activity. It is believed that, through the use of immune regulating or immune modulating molecules, a state of general immune system hyperactivity can be induced which may help combat challenges to the immune system (e.g., pathogenic infection). Such infection may arise from a wound site or may arise from an opportunistic blooming when the host organism is simply deprived of sufficient sleep. It is believed that an induced state of general immune hyperactivity would result in a therapeutic response to the challenge. This might be viewed as the opposite of the vaccination type response that produces a specific long-term immunity. If such a non-specific immune response could be initiated at will it could be utilized to either act alone or in conjunction with a conventional treatment directed towards the etiological agents.

Such a mechanism could be based upon activation of phagocytic cells that are capable of responding to a wide range of infectious agents. It may also be that the T-lymphocytes, which are major mediators of the overall immune response, may act to enhance the operation of non-specific cellular immunity even though the T-lymphocytes themselves are a part of the specific immune response.

The search for agents which potentiate the immune response is a driving force in drug research. Cytokines and cationic peptides are two classes of "relatively" low molecular weight compounds which have shown promise in this area of research. At least nine immuno-defense peptide products are commercially available with annual sales of over $4 billion (Latham, P. W., 1999, Therapeutic peptides revisited, *Nature Biotechnology* 17:755–757).

Bio-active peptides (such as "cationic peptides") are emerging as promising alternatives for combating antibiotic-resistant bacteria with minimum inhibitory concentrations reported from 1–100 µg/ml Martin, A, T. Ganz, and R. I. Lehrer, 1995. Defensins and other endogenous peptide antibiotics of vertebrates. *J. Leukoc. Biol.*, 58:128–136; Hancock, R. E. W., 1997, Peptide antibiotics, *Lancet*, 349:418–422). Cationic peptides range from 16–18 amino acid residues for the protegrins (Ganz, T., and R. Lehrer, 1998. Antimicrobial peptides of vertebrates, *Curr. Opi. Immunol.*, 10:41–44.) to 29–35 residues for mammalian defensins (Sawa, T, and K. Turahashi, 1999, Antimicrobial peptides/proteins application to the therapy of sepsis (article in Japanese), Masui, 48:1186–1193.). Due to a compositional prominence of lysine and arginine, they possess a net positive charge of at least 2, and usually 4, 5, or 6 (Hancock, R. L. W., 1997, Peptide antibiotics, *Lancet*, 349:418–422).

Interleukin-1 (IL-1), tumor necrosis factor-α (TNF-α) and interferon (IFN) are three cytokines which participate in the immune response IL-1 is involved in the host's response to antigenic challenge and tissue injury, and has been shown to increase the resistance of mice to pathogenic organisms such as Listeria, *Escherichia coli,* and *Candida albicans* (Czuprynski, C. J., and Brown, J. F., 1987, Recombinant murine interleukin-1α enhancement of nonspecific antibacterial resistance, *Infection and Immunity* 55:2061–2065; Cross, A. S., Sadoff, J. C., Kelly, N, Bermton, F., and Gemski, P, 1989, Pretreatment with recombinant murine tumor necrosis factor α/cachectin and murine interleukin 1α protects mice from lethal bacterial infection, *The Journal of Experimental Medicine* 169:2021–2027; Pecyk, R. A., Fraser-Smith, E. B., and Matthews, T. R., 1989, Efficacy of interleukin-1β against systemic *Candida albicans* in normal and immunosuppressed mice, *Infection and Immunity* 57:3257–3258.). TNF-α and γ-IFN were able to increase the resistance of mice to *Salmonella typhimurium* (Morrissey, P. J., and Chamer, K., 1994, Treatment of mice with IL-1 before infection with increases resistance to a lethal challenge with *Salmonella typhimurium, The Journal of Immunology* 153:212–219). Human a IFN's have potent antiviral and antiproliferative activities, and are currently being utilized as anticancer or antiviral therapeutic agents (Chang, C. J., Chen, T. T., Cox, B. W., Dawes, G. N., Stemmer, W., Punnonen, J., and Patten, P. A., 1999, Evolution of a cytokine using DNA family shuffling, *Nature Biotechnology* 17:793–797).

Cationic peptides help defend against the constant assault of moderate numbers of bacteria. Each natural peptide has a broad but incomplete spectrum of activity. The host compensates for this by producing an array of different peptides that together have a broader spectrum of activity, and often work in synergy with one another. A single individual may produce dozens of different peptides and more than 500 natural cationic peptides have been discovered (Hancock, R. E. W., 1999. Host defence (cationic) peptides *Drugs* 57:469–473).

Bio-active peptides have been found to possess antiviral, antibacterial, antifungal, and wound healing properties (Sanglier, J., Haag, H., Huck, T., and Fehr, T, 1993. Novel bioactive components from Actinomycetes: A short review (1988–1992). *Res. Microbiol.* 144:633–642; Mizuno, T., Wang, G., Zhang, J., Kawagishi, H., Nishitoba, T., and Li, J, 1995, Reishi, *Ganoderma Lucidum* and *Ganoderma Tsugar.* Bioactive substances and medicinal effects, *Food Rev. Int.* 11:151–166; Hancock, R. E. W., 1999. Host defence (cationic) peptides *Drugs* 57:469–473). A decameric peptide has even been shown to impede the growth and spread of established tumors (Folkman, J., 1999, Angiogenic zip code, *Nature Biotechnology* 17:749). It is believed that these "defense" peptides are more general in action than antibodies, and as such, have a broader range of activity (Hancock, 1999). These peptides have low toxicity to most mammalian cells and are therefore candidates for development as therapeutic agents (Maloy, W. L., and U. P. Kari, 1995. Structure-activity studies on magainins and other host defense peptides, *Biopolymers (Peptide Science)* 37:105–122).

Mammalian species used as food animals are subjected to high stress levels during shipment to processing centers and while awaiting processing. Disease is common during such periods of stress.

In addition to food animals, numerous mammalian species such as dogs, cats and other non-food animals are maintained as pets and are subject to various diseases where an immune stimulant would be desirable.

Equine species are susceptible to diseases which are capable of being beneficially treated using immune stimulants.

More exotic mammals, such as those kept in zoos, are subject to stress related and stress non-related diseases due to the artificial environments in which they live. A nonspecific immunomodulator would be desirable for both prophylactic and ameliorative purposes.

The cost associated with the administration of prophylactic ants and the inherent risk of residues of such drugs, remaining in the edible portions of a food animal make it desirable to minimize the administration of such drugs. A simple and elegant means of accomplishing this is to increase the assertiveness of the mammals own disease fighting immune system.

Therefore, it is an object of the present invention to provide a means for modulating the immune response in mammals afflicted with disease.

Another object of the present invention is to provide a means for enhancing the ability of conventional antimicrobial medicaments by providing a concomitant stimulation of the mammal's immune response.

Yet another object of the present invention is to provide a means of stimulating the immune response in mammals to heighten the mammals ability at self-healing when a challenged by an infectious agent.

Yet another object of the present invention is to provide a means of prophylactically stimulating the immune response in mammals to heighten the animal's ability to avoid disease prior to being placed in a high stress environment.

Yet another object of the present invention is to provide a means of stimulating the immune response in mammals to heighten the animal's ability to respond to sub-clinical disease conditions.

It is also an object of the present invention to non-specifically stimulate the immune system of a mammal by removing and fractionating a portion of the mammals blood, storing the low molecular weight fraction until required and re-introducing the fraction into the donor mammal when required either prophylactically or after a disease state has commenced.

The above and further objects and novel features of the invention will more fully appear from the following description and the examples contained therein.

SUMMARY OF THE INVENTION

Figure 1:
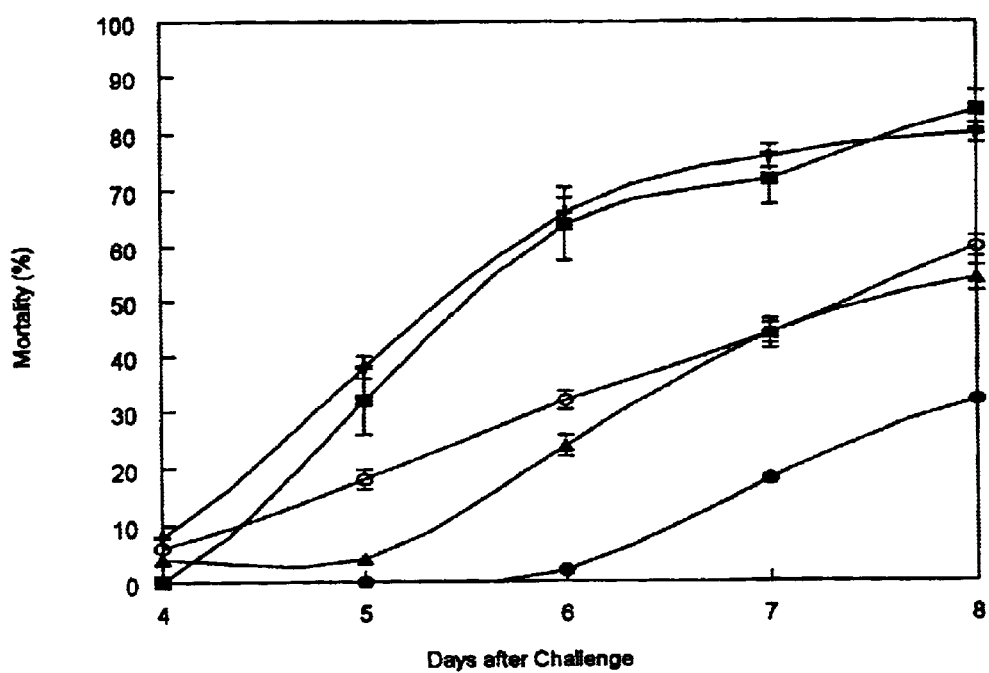
FIG. 1 shows the effect of administration of CSF-I2 at different times. Control mice were administered 0.1 ml (~5×10³ CFU) of *S. typhimurium* i.p. on day 0 (+), while treated mice received both *S. typhimurium* on day 0 and a 0.1 ml subcutaneous injection of CSF-I2 (5 mg) either on day −4 (■), day −2 (○), day −1 (●), or day 0 (▲). Each data point represents the average daily mortality (n=5) per cage of 5 mice.

Surprisingly, I have now determined that substantially immunoglobulin free material fractionated from mammalian serum, preferably goat serum, helps retard pathogenesis in mammalian species.

The inventive method and inventive compounds derived thereby involve, generally, the isolation of a low molecular weight substantially immunoglobulin free material from the blood of a mammal. This mamma has not been pre-treated in any way nor have foreign antigens been artificially introduced to the mammal. The substantially immunoglobulin free fraction obtained from this mammal is then used to treat a mammal. The mammal can be any mammalian species and may be the same species as the fraction donor or may be a different species. The recipient and the donor mammal may be the same individual.

Treatment of the mammal with the substantially immunoglobulin free fraction from the mammalian donor stimulates the immune system of the recipient mammal. The mammal is thereby assisted in overcoming the deleterious effects of a disease or malady.

The present invention is broadly concerned with unique products and methods for cross species modulation of the immune system. Although not intended as a limitation on this disclosure, it is presently believed that treating a mammal with the composition of the present invention stimulates the immune system response in the mammal by inducing macrophages, T-lymphocytes and natural killer cells. Thus the subject animal is able to ward off the deleterious effects of a challenge by the infectious microorganism.

DETAILED DESCRIPTION

Substantially or completely immunoglobulin free material fractionated from mammalian serum, preferably goat serum, helps retard pathogenesis in mammals, supporting the belief that the substantially immunoglobulin free fraction is a non-specific species independent immunomodulator.

Agents which retard pathogenesis may enable a host to mount a successful defense to challenges of the immune system. These agents can provide specific protection (i.e., in the form of antibodies) or be general in nature and enhance the overall immuno-response. Cytokines and cationic peptides are two such classes of non-specific defense agents.

The product of this invention is an immunomodulator derived from mammalian serum and which contains a mixture of serum proteins or completely free of immunoglobulins. The immunomodulator may be adjuvanted or non-adjuvanted. Preferably it is non-adjuvanted. The mammalian species is preferably one from which relatively large quantities of blood may be drawn. Goats are a preferred source for serum.

Albumin and immunoglobulins (the two most abundant serum proteins) have molecular weights in the range of 66,000 to 155,000 daltons. The product of this invention may be produced utilizing a size fractionation procedure to remove proteins and other molecules having a molecular weight greater than 60,000 daltons, preferably greater than 25,000 daltons, most preferably greater than 8,000 daltons. Therefore, the product is substantially if not completely free of immunoglobin, albumin, and most cytokines. However, the presence of minor amounts of high molecular weight components does not diminish the effectiveness of the low molecular weight components in ameliorating diseases in mammals Such high molecular weight components may however engender undesirable side effects when present and it is thus preferable that they not be present.

The mammalian serum suitable for use in the invention is obtained from any convenient species of mammal. It is convenient to use large animals to obtain greater quantities of serum It is convenient to use domestic animals as they are readily available. Thus, convenient species are horses, cows, goats, sheep and pigs. Horses and goats are preferred sources; goats are the most preferred serum source.

The collected serum is treated to separate it into high and low molecular weight fractions. A convenient cut-off point for the separation is in the range of 6000–8000 daltons although any cut-off point which effectively excludes immunoglobulins is acceptable. The primary requirement is that the fractionation remove substantially all immunoglobulins and albumin present from the low molecular weight fraction.

The serum may be fractioned in any convenient manner. It is desirable to fractionate the material by collecting the material which flows through a dialysis membrane possessing the desired molecular weight cut-off range. Spectra Por™ dialysis membranes with appropriate cut-off limits have been used successfully in preparing the products of this invention. Alternative fractionation procedures may also be used, provided that they remove serum fractions having a molecular weight cut-off of over 60,000 daltons, preferably over 25,000 daltons, most preferably over 8,000 daltons, and do not denature the peptides in the low molecular weight portion.

The low molecular weight material obtained from the fractionation process may be used immediately or it may be held for future use. If held for future use it is conveniently lyophilized to a powder and stored at −70° C., until reconstituted with water for use. A typical fraction derived from goat serum has a proteinaceous content of 35%–40% based on an analysis of its nitrogen content.

The non-specific immunomodulator of this invention may be wed to protect mammals against the onset of diseases or may be utilized to ameliorate the effect of diseases after they begin.

The immunomodulator has demonstrated useful protective properties in various species of mammals, such as dogs, cats, horses, sheep, pigs and cows. It can provide prophylactic or curative effects against such varied bacterial or viral diseases as mastitis and shipping-fever in cows; enteritis, respiratory disease and shipping fever in pigs; upper respiratory disease, feline leukemia and viral encephalopathy in cats; parvovitus, demedex mange, distemper and kennel cough in dogs; and papillomas, sarcoids, respiratory infection and lower airway disease in horses.

The product has an tended shelf life as a lyophilized powder. The lyophilized product has a protein content of approximately 37.5% as determined by its nitrogen content The lyophilized product may be reconstituted with distilled water to provide a product having a solids content of any convenient amount. For convenience, it is preferable to utilize material having a solids content of between about 0.1 mg/ml to about 20 mg/ml preferably from about 1 to about 15 mg/ml and most preferably from about 1.5 to about 10 mg/ml.

The treatment regime will vary with the animal and purpose of administration. A second dose of the same size is typically administered between 3 and 10 days after the first dose. In most cases, the therapeutic benefit is dose dependent and the most significant therapeutic result are obtained above a minimum threshold amount. The effective dose is, in general, determined by the weight of the animal being treated. Dosage amounts depend on the size of the animal being treated and range from about 0.25 mg in cats to about 3.0 mg in horses and cows. The dose will tend toward the low end when the animal is small and toward to high end when the animal is large.

The duration of the products therapeutic effect varies depending on the animal and the challenge. In general, the product demonstrates a marked therapeutic effect when administered no sooner than 4 days pre-challenge. Best results are generally obtained when CSF-I2 is administered no sooner than 2 days before challenge.

The material may be administered alone, in conjunction with, at the same time as, or shortly before or after other treatments.

The material may be administered by any convenient route, such as intramuscularly, subcutaneously, intravenously or intraperitoneally. Topical administration, with a suitable adjuvant such as DMSO, is also effective against certain conditions. Oral administration is of particular usefulness for small or non-domesticated mammals.

This low molecular weight material (CSF-I2) was subjected to testing to determine its ability to prevent the growth of bacteria. The results obtained show that the material is unable to inhibit growth of gram-negative or gram-positive bacteria.

The material has been tested in various species of mammals and has been determined to be effective in lessening or curing various diseases either when used alone or in conjunction with standard therapies. The material has demonstrated especial efficacy in canine, feline, equine, and bovine species. It is effective against parvovirus, kennel cough and enteritis, upper respiratory disease, papillomas, sarcoid tumors and respiratory infection. It is effective against both bacterial and viral challenges.

In addition to field testing of the efficacy of the inventive compositions against various disease challenges in multiple mammalian species, a mouse model was developed to more easily, quickly and inexpensively characterize and determine the efficacy of the novel compositions' therapeutic benefits.

Six-week old, female Swiss Webster mice were injected intraperitoneally (i.p.) with *Salmonella typhimurium* on day 0 (~$5.00\times10^3$ bacteria/mouse), effectively establishing an $LD_{80}$ 7 to 8 days post-challenge. Treated mice were infected with *S. typhimurium*, but were also given a subcutaneous injection of CSF-I2. Mortality was compared between the control and treated groups. Studies were also performed in this manner to determine the optimal time of CSF-I2 administration and the CSF-I2 dose response profile.

EXAMPLE 1

To determine the level of effectiveness of the low molecular weight compositions of this invention in ameliorating disease states in mammalian species, mice were pathogenically challenged.

Animal Husbandry

Four-week old, female Swiss Webster mice were obtained from Charles River laboratories (Wilmington, Mass.). The mice were acclimated for 2 weeks, during which time they were fed a standard maintenance diet, Laboratory Rodent Diet 5001 (PMI Feeds, Inc.), and watered ad libitum. Mice were group-housed (5 mice per cage) in plastic boxes bedded with wood shavings. Mice were transferred to an isolation room immediately after inoculation with *S. typhumurium*. The isolation room was maintained at 20° C. in a controlled negative pressure environment on a 12-hour lighting cycle.

Bacteria

*Salmonella typhumurium* (ATCC 14028) was used as the challenge organism after passaging three times through a murine host with subsequent isolation and stored in phosphate buffered saline with 10% glycerol at −80° C. This isolate was supplied from a stock culture from the Department of Biological Sciences (Mississippi State University) where it is maintained as a reference organism. Culture rehydration and cryoprotective maintenance conditions have been described previously (Darnell, K. R. Hart, M. E., and Champlin, F. R., 1987, Variability of cell surface hydrophobicity among *Pasteurella multocida* somatic serotype and *Actinobacillus lignieresii* strains. *J. Clin. Microbiol.* 25:67–71.), Journal of Clinical Microbiology 25:67–71).

Preparation of Caprine Serum Fraction (CSF-I2)

Goat serum was fractioned by collecting that material which flowed through a dialysis membrane (Spectra Por) possessing a molecular weight cut-off of 68,000 daltons. The low molecular weight material (CSF-I2) was lyophilized to a powder and stored at −70° C., until reconstituted with water for use. CSF-I2 was determined to be 37.5% proteinaceous based on its nitrogen content.

Bacterial Susceptibility Assays

Caprine serum and its high (over 8,000 daltons) and low molecular weight (less than 8,000 daltons) subfractions (each at a protein concentration of 20 mg/mL) were assessed for antimicrobial activity against both gram positive and ram negative bacteria by performing disk agar diffusion assays as described in Hart, M. E., and Champlin, F. R., 1988, and *Actinobacillus lignieresii, Antimicrobial Agents and Chemotherapy* 32:1354–1359).

Antibiotic minimum inhibitory concentrations (MICs) were determined in Mueller-Hinton broth (Difco Laboratories, Detroit, Mich.) using the broth dilution method described previously (Darnel, K. R., Hart, M. E., and Champlin, F. R., 1987, Variability of cell surface hydrophobicity among *Pasteurella multocida* somatic serotype and *Actinobacillus lignieresii* strains, *Journal of Clinical Microbiology* 25:67–71).

Caprine serum and its dialysate containing immunoglobulins (over 8,000 daltons) were unable to inhibit bacterial growth. CSF-I2, material presumed to contain small molecular weight immunostimulatory agents, also failed to inhibit the growth of all test bacteria, including two serotypes of Pasteurella (Table I).

The minimum inhibitory concentration (MIC) for a cationic peptide is usually in the range of 1 to 8 μg/mL (Mancock, R. E. W., 1997, Peptide antibiotics, The Lancet 349:418–422). Two serotypes of Pasteurella showed no zone of growth inhibition when CSF-I2 was tested at 20 mg/mL, over 2,500 times the upper MIC range recognized for cationic peptides, however, the product was able to inhibit Pasteurella pathogenesis in avian studies.

TABLE I

Susceptibility Of Selected Bacteria To Growth Inhibition By Caprine Serum Fractionated Into Its High (>8,000 Daltons) And Low (<8,000 Daltons) Molecular Weight Components.

| | [a]Zone of Inhibition | | | |
|---|---|---|---|---|
| | Low MW | | High MW | |
| Organism | 4 hr | 24 hr | 4 hr | 24 hr |
| Gram Negative Bacteria | | | | |
| Pseudomonas aeruginosa ATCC 27853 | 0 | 0 | 0 | 0 |
| Pseudomonas aeruginosa PAO1 | 0 | 0 | 0 | 0 |
| Escherichia coli ATCC 25922 | 0 | 0 | 0 | 0 |
| Enterobacter aerogenes | 0 | 0 | 0 | 0 |
| Enterobacter cloacae | 0 | 0 | 0 | 0 |
| Salmonella typhimurium | 0 | 0 | 0 | 0 |
| Pasteurella multocida ATCC 11039 | [b]IG | 0 | IG | 0 |
| Pasteurella multocida P-1581 | IG | 0 | IG | 0 |
| Gram Positive Bacteria | | | | |
| Staphylococcus aureus | 0 | 0 | 0 | 0 |
| Staphylococcus aureus T-5706 | 0 | 0 | 0 | 0 |
| Bacillus subtilis | IG | 0 | IG | 0 |

[a]MHA plates were streak inoculated with each of the assay organisms. Sterile filter paper disks impregnated with either the high or low MW caprine serum fraction were aseptically applied to the seeded plate surfaces. The plates were incubated for 24 h at 37° C., during which time inhibition of growth in areas surrounding the disks were visually assessed at 4 and 24 hr.
[b]IG, insufficient growth.

Mouse Treatment

Mice comprising the control and treated populations were injected i.p. with 0.1 ml of *Salmonella typhimurium* (~5.00× $10^3$ bacteria/mouse) on day 0. Unless stated otherwise, treated mice were given a 0.25 ml subcutaneous injection of CSF-I2 (20 mg/ml at the time designated by the experimental protocol, while control mice received a placebo of physiological saline. Negative control mice were sham handled in a similar manner to the control and treated populations to evaluate the influence of non-experimental parameters on mortality. To obtain statistical significance, mice were housed five per cage and a minimum of five cages were used per treatment group. Mice were monitored three times daily and mortality recorded until 80% of the control mice died or for a maximum of two weeks.

Statistical Analysis

All experiments were arranged in a completely randomized design. Data demonstrating cumulative mortality were analyzed using one way analysis of variance (ANOVA) with the general linear models procedure (Proc GLK and the means separated by Fisher's projected LSD procedure (SAS Institute Inc., SAS/STAT® User's Guide, Version 6, Fourth Edition, Volume 2, Cary, N.C.: SAS Institute Inc., 1989). A p value less than 0.05 was necessary to be considered significant.

EXAMPLE 1

A single dose of CSF-I2 was administered at various times prior to challenge to assess persistence of it's positive effects and to ascertain the optimal time of its administration with regard to the *S. typhimurium* challenge model.

CSF-I2 was administered on either day −4, −2, −1, or coincident with the challenge on day 0 (FIG. 1). Four days were usually required before deaths were observed in control populations of female Swiss Webster mice challenged with *S. typhimurium* (~5×$10^3$ bacteria/mouse). A rapid rise in death ensued with an $LD_{80}$ occurring 8 days post challenge. Mice treated with CSF-I2 four days prior to challenge showed no significant difference from this pattern. Benefit, however, was observed if CSP-I2 was given on either day −2 or 0.

By day 8 the control population presented 80% mortality, while groups that received CSF-I2 on either day −2 or 0 had mortalities of 60% and 54%, respectively. Mice treated one day prior to challenge had the least number of deaths. Only 18% and 32% of this treated group were dead at days 7 and 8 post challenge, respectively.

Beginning with day 5 post-challenge (when mortality was established in the control population) there was a statistically significant difference between the control group and each of the day −2, −1, and 0 CSF-I2 treated groups. The day −1 treatment group was also significantly different from the day 0 and day −2 CSP-I2 populations. These results demonstrate that the administration of CSF-I2 reduces the mortality of the challenged animals.

EXAMPLE 2

Figure 2:
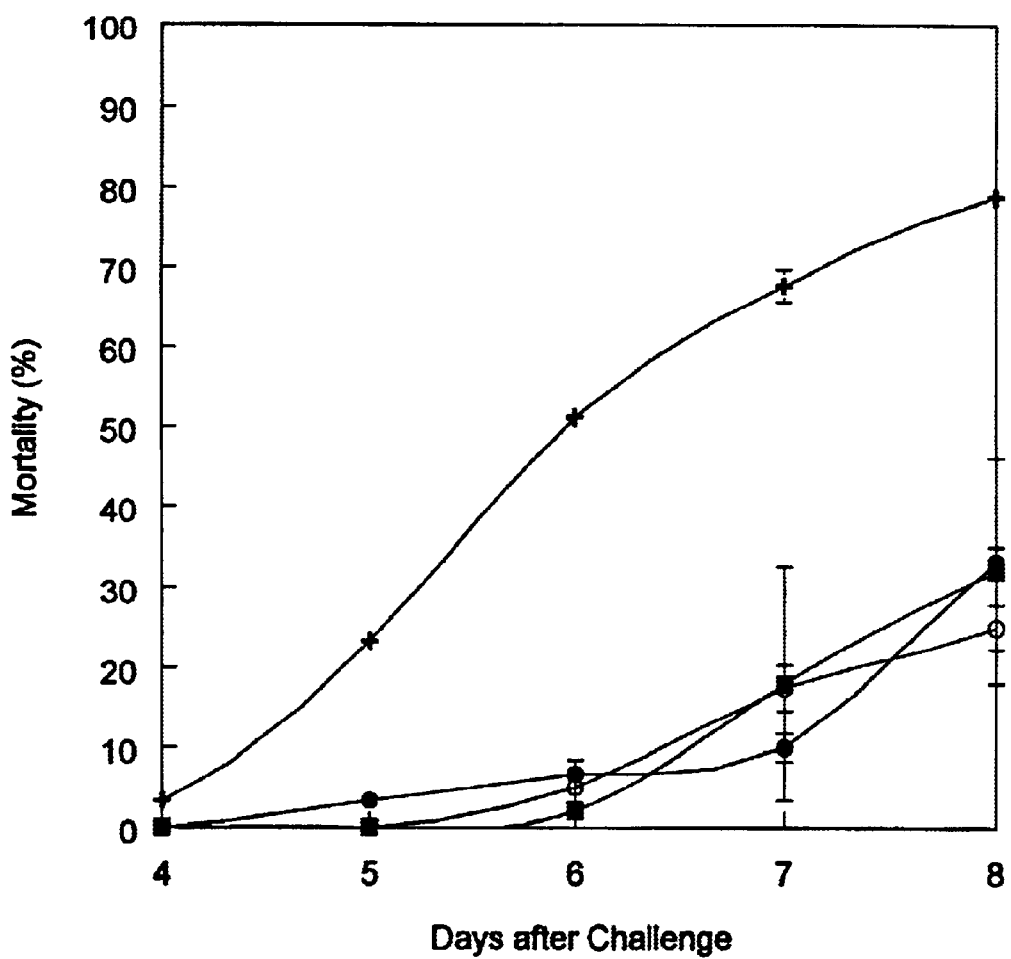
FIG. 2 shows the effect of Post-Challenge Administration of CSF-I. Control mice were administered 0.1 ml (~5×10³ CFU) of *S. typhimurium* i.p. on day 0 (+), while treated mice received both *S. typhimurium* on day 0 and a 0.25 ml subcutaneous injection of CSF-I2 (5 mg) on either day −1 (■), days −1 and 1 (○), or on days −1 and 2 (●). Each data point represents the average daily mortality (n=6) per cage of 5 mice.

The effect of supplemental administrations of CSF-I2 on survival was determined. Control mice were compared to three treated groups: one which received a single 5 mg dose of CSF-I2 on day −1 and two groups which received two 5 mg doses of CSF-I2 on day −1 and 1, or day −1 and 2 (FIG. 2).

Onset of mortality occurred approximately 4 days post-challenge. All treated groups had significantly fewer deaths than the control population between days 5 and 8. Approximately 50% fewer deaths were observed 7 to 8 days post-challenge for all groups of mice treated with CSF-I2. Additional therapeutic benefit as rendered by multiple CSF-I2 administrations was not discernable within the experimental structure.

These results demonstrate that there is no significant difference in therapeutic benefit in multiple administrations of CSF-I2 after maximal stimulation has been achieved. This does not negate however the possibility of hyperstimulating the immune system in a successive manner once the initial administration of CSF-I2 is found to dissipate.

EXAMPLE 3

Figure 3:
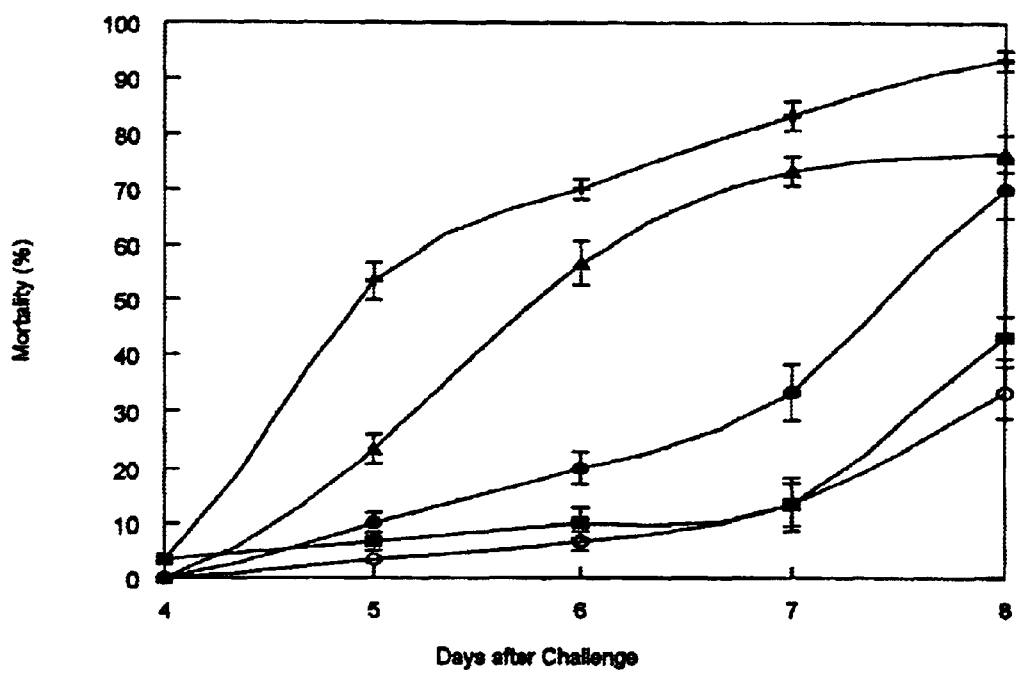
FIG. 3 shows the CSF-I2 dose response profile. Control mice were administered 0.1 ml (~5×10³ CFU) of *S. typhimurium* i.p. on day 0 (+), while treated mice received both *S. typhimurium* on day 0 and a subcutaneous injection of either 20.0 mg (■), 15.0 mg (○), 5.0 mg (●) or 0.1 mg (▲) CSF-I2. Each data point represents the average daily mortality (n=6) per cage of 5 mice.

A dose response study was performed in order to determine the optimal amount of CSF-I2 to administer for prevention of mortality (FIG. 3). CSF-I2 was prepared so that a 0.25 to 0.5 ml i.p. injection would deliver either 0.1, 5, 15, or 20 mg CSF-I2. All injections of CSF-I2 were given on day −1, as this was shown by the time course study to produce the greatest therapeutic benefit. On day 7, all doses were significantly different (p<0.05) from the control mice except for the 0.1 mg CSF-I2 dosage. Eighty three percent of the control population died by day 7, while with respect to increasing amounts of CSF-I2, 73.3, 33.3, 13.3, and 13.3% had died in these treated groups.

EXAMPLE 4

CSF-I2 was incubated at 37° C. for 30 minutes. The material no longer provided therapeutic benefit.

CSF-I2 was treated with Bromelain (nonspecific endoprotease—3.6 units in 10 ml and 2 mg/ml Proteinase K, left at room temperature and agitated periodically for 24 hours. The material no longer provided therapeutic benefit, establishing the proteinaceous nature of the bio-active component(s).

EXAMPLES 5–38

Field trials of the immunomodulator were conducted in a number of animal clinics to determine the field effectiveness of the CSF-I2 treatment. The immunomodulator was administered by clinical investigators who were licensed veterinarians. The trials were conducted with various mammals including dogs, cats, horses and cows. The effect of administration of CSF-I2 on animals evidencing various disease syndromes was demonstrated by administering appropriate doses of CSF-I2 to animals having URD [upper respiratory disease], CRD [chronic respiratory disease], parvovirus, papillomas, sarcoids and mastitis.

In animals 5, 15–22 and 36–38 the immunomodulator was administered in conjunction with one or more antibiotics or other medicaments typically used in treating such diseases.

The standard recognized treatment regimes for the listed disease syndromes is treatment with antibiotics for 10 to 12 days [URD, CRD, parvovirus] or by surgically excising the growths [papillomas and sarcoids].

The treatment regime when using CSF-I2 either alone or in conjunction with antibiotics is from 3 to 6 days with a first dose on day and a second dose, if required, on day 3 or 4 [in example 10 a third dose was administered on day 6].

The results are listed in Table 2 and demonstrate the efficacy of CSF-I2 in various mammalian species and various disease states.

TABLE 2

| Animal No. | Animal | Breed | Sex, Age, Weight [lbs.] | Complaint/ Diagnosis | Duration of Illness | Severity | Dose Administered | Administration Route | Improvement | Follow up Treatment | Two Dose Results |
|---|---|---|---|---|---|---|---|---|---|---|---|
| 5* | Canine | Dachshund | M, 11 wk., 8 | Parvovirus | 4 days | Severe | 0.5 ml | IM | Great | | Cured |
| 6 | | Husky Cross | F, 12 wk., 35 | Parvovirus | 3 days | Severe | 0.5 ml | IM | Great | none | |
| 7 | | GSD | F, 4 mo. 25 | Kennel Cough | 3 days | Moderate | 0.5 ml | Subcu | Moderate | 0.5 ml | Cured |
| 8 | | Golden Ret. Mix | M, 1 yr., 55 | Kennel Cough | 4 days | Moderate | 0.5 ml | Subcu | Moderate | 0.5 ml | Cured |
| 9 | | Dalmation | F, 6 mo., 28 | Kennel cough | 4 days | Moderate | 0.5 ml | Subcu | | 0.5 ml | Cured |
| 10 | | Brittany Mix | M, 9 wk., 8 | Diarrhea & Kennel Cough | 2 days | Severe | 0.25 ml | IM | Great | 0.25 ml | 3rd dose, Great |
| 11 | | GSD | F, 1 yr., 55 | Kennel Cough | 3 days | Moderate | 0.5 ml | IM | Moderate | 0.5 ml Subcu | Cured |
| 12 | | Husky Cross | F, 4 yr., 40 | Kennel Cough | 4 days | Moderate | 0.5 ml | IM | Great | 0.5 ml | Cured |
| 13 | | Sch. | M, 6 yr., 14 | Kennel Cough | 7 days | Mild | 0.5 ml | Subcu | Moderate | 0.5 ml | Cured |
| 14 | | Labrador | F, 4 mo., 25 | Kennel Cough | 5 days | Mild | 0.35 ml | IM | Cured | none | |
| 15* | Equine | QH | G, 9, 1150 | CRD | >30 days | Moderate | 1.0 ml | IM | Moderate | 1.0 ml | Great |
| 16* | | QH | G, 7, 1200 | CRD | >30 days | Severe | 1.0 ml | IM | Moderate | 1.0 ml | Great |
| 17* | | QH | G, 3, 1150 | CRD | >14 days | Mild | 1.0 ml | IM | Moderate | 1.0 ml | Great |
| 18* | | QH | F, 2, 980 | CRD | 21 days | Mild | 1.0 ml | IM | Great | 1.0 ml | Cured |
| 19* | | Paine | G, ?, 1100 | CRD | >30 days | Severe | 1.0 ml | IM | Moderate | 1.0 ml | Great |
| 20* | | QH | G, 3, 1100 | CRD | >30 days | Chronic | 1.0 ml | IM | Great | 1.0 ml | Great |
| 21* | | Thoroughbred | G, 2, 1050 | CRD | >30 days | Moderate | 1.0 ml | IM | Great | 1.0 ml | Great |
| 22* | | QH | G, 15, 1100 | CRD | >30 days | Chronic | 1.0 ml | IM | Moderate | 1.0 ml | Great |
| 23 | | QH | G, 2, 950 | Papillomas | Unknown | moderate | 1.0 ml | IM | ? | 1.0 ml | Great |
| 24 | | QH | G, 7, 1000 | Sarcoid | >60 days | moderate | 1.0 ml | IM | none | 1.0 ml | Great |
| 25 | | QH | G, 10, 1150 | Sarcoid | >90 days | Moderate | 1.0 ml | IM | ? | 1.0 ml | Great |
| 26 | Feline | DLH | F, 9 wk., 2 | URD | 14 days | Mild | 0.25 | IM | Moderate | 0.25 | Cured |
| 27 | | DSH | M, 3 yr., 8 | URD | 7 days | Moderate | 0.25 | IM | Moderate | 0.25 | Great |
| 28 | | DSH | M, 4 yr., 8 | URD | 10 days | Life threatening | 0.5 | IM | Cured | none | |
| 29 | | DLH | F, 8 wk., 1 | URD | 7 days | moderate | 0.25 | IM | Moderate | 0.25 Subcu | Great |
| 30 | | DSH | F, 1 yr., 8 | URD | 7 | moderate | 0.5 | IM | Moderate | 0.5 | Cured |
| 31 | | DSH | M, 4 yr., 10 | URD | 10 days | Severe | 0.5 | IM | Great | 0.5 | Cured |
| 32 | | DSH | M, 2 yr., 9 | URD | 14 days | Moderate | 0.5 | IM | Moderate | 0.5 | Moderate |
| 33 | | DSH | M, 1 yr., 10 | URD | 10 days | Severe | 0.5 | IM | Great | 0.5 | Cured |
| 34 | | DSH | M, 1 yr., 9 | URD | 14 days | Moderate | 0.5 | IM | Moderate | 0.5 | Great |
| 35 | | DSH | F, 6 wk., 1.5 | URD | 5 days | Severe | 0.25 | IM | Moderate | 0.25 | Moderate |
| 36* | Bovine | Holstein | F, 4 yr., 1000 | Mastitis | 4 days | Severe | 4 ml | IM | Cured | none | |
| 37* | | Holstein | F, 4 yr., 1000 | Mastitis | 3 days | Severe | 4 ml | IM | Cured | none | |
| 38* | | Holstein | F, 4 yr., 1000 | Mastitis | 3 days | Moderate | 4 ml | IM | Cured | none | |

*ancilliary treatment provided.
URD - upper respiratory disease
CRD - chronic respiratory disease

EXAMPLE 39

CSF-I2 was fractionated from the blood of various mammalian species and tested for efficacy under the conditions set forth above. Thirty mice were challenged with Salmonella, $5.4 \times 10^3$ bacteria/mouse injected i.p. and received doses of 5 mg of CSP-I2 as a 0.25 ml subcutaneous injection of 20 mg/ml CSF-I2 on days −1 and 0. The results are recorded below.

| Source | Time of Administration | % Mortality on day 6 |
| --- | --- | --- |
| Goat D1 | administered on day −1, 0 | 0 |
| Bovine D1 | administered on day −1, 0 | 36.7 |
| Equine D1 | administered on day −1, 0 | 3.3 |
| Canine D1 | administered on day −1, 0 | 6.7 |
| Control | Salmonella, $5.4 \times 10^3$ bacteria/mouse | 90 |

I claim:

1. A method for the inmunostimulation of a mammal wherein a therapeutically effective amount of a composition of matter comprising those components of the blood of a first mammal which have a molecular weight of less than 60,000 daltons and which is substantially free of components having a molecular weight of greater than 60,000 daltons is administered to a second mammal.

2. The method of claim 1 where the second mammal is a member of the canine family and the disease state is parvovirus, demedex mange, distemper or kennel cough.

3. The method of claim 2 where the second mammal is a member of the canine family and the disease state is parvovirus.

4. The method of claim 1 where the second mammal is a member of the bovine family and the disease state is mastitis or shipping fever.

5. The method of claim 1 where the second mammal is a member of the porcine family and the disease state is enteritis, respiratory disease, or shipping fever.

6. The method of claim 1 where the second mammal is a member of the feline family and the disease state is upper respiratory disease, feline leukemia, or vital encephalopathy.

7. The method of claim 1 where the second mammal is a member of the equine family and the disease state is papillomas, sarcoids, respiratory infection or lower airway disease.

\* \* \* \* \*